United States Patent [19]

Schuler

[11] Patent Number: 4,666,111
[45] Date of Patent: May 19, 1987

[54] HOLDER FOR IV TUBE

[76] Inventor: Robert Schuler, 79 Heatherhill La., Woodcliff Lake, N.J. 07675

[21] Appl. No.: 798,016

[22] Filed: Nov. 14, 1985

[51] Int. Cl.⁴ ............................................. A47G 29/00
[52] U.S. Cl. ................................. 248/125; 248/231.7
[58] Field of Search ............ 248/125, 121, 122, 231.7, 248/295.1, 245, 75; 211/107, 113, 117; 128/DIG. 3, DIG. 26, DIG. 6

[56] References Cited

U.S. PATENT DOCUMENTS

| | | | |
|---|---|---|---|
| 225,020 | 3/1880 | Pettengill | 248/318 |
| 1,327,749 | 1/1920 | Whipp | 248/125 X |
| 2,202,265 | 5/1940 | Phillips | 248/125 |
| 2,554,544 | 5/1951 | Warner | 248/231.7 X |
| 2,948,450 | 8/1960 | Dobrikin | 248/75 |
| 3,709,372 | 1/1973 | Alexander | 248/318 |
| 4,030,690 | 6/1977 | Hanaver et al. | 248/125 X |
| 4,225,104 | 9/1980 | Larson | 248/125 |
| 4,262,872 | 4/1981 | Kodet | 248/318 X |
| 4,332,378 | 6/1982 | Pryor | 248/125 X |
| 4,383,252 | 5/1983 | Purcell | 248/75 X |

Primary Examiner—J. Franklin Foss
Attorney, Agent, or Firm—Michael J. Striker

[57] ABSTRACT

An IV holder is used in combination with an IV stand having a post, an IV-liquid supply on the stand, and a tube extending from the supply to a recumbent patient adjacent the stand. The holder comprises a clamp body releasably secured to the post, an elongated pole having an inner end fixed to the clamp body and an outer end and extending horizontally from the clamp body and post, and a spring on the outer end of the pole connected to the IV tube between the patient and the supply and holding the tube up in the air above the patient. The outer end of the pole is above the patient, to which end the pole is at least 24 in long. In addition the spring is a tension spring having an upper end secured to the outer end of the pole and a lower end releasably secured to the tube. This spring is stiff enough so that it can hold up the tube, but not so stiff that it prevents the tube from being pulled freely down.

8 Claims, 4 Drawing Figures 4,666,111

HOLDER FOR IV TUBE

FIELD OF THE INVENTION

The present invention relates to an accessory for use with an intravenous (IV) stand. More particularly this invention concerns a device for holding the tube extending from the liquid supply of the stand to the patient.

BACKGROUND OF THE INVENTION

An IV stand comprises an upright post having at its top a traverse from which supply bags or bottles of IV liquid —normally blood or saline solution—are suspended. A thin tube extends from these supplies to a needle implanted in the wrist or hand of the patient who typically is recumbent in a bed adjacent the stand. Flow may be by gravity through the tube, or a peristaltic-type IV pump may be provided for accurately controlling and metering flow.

A problem with such devices is that the tube often trails from the patient over the bed and thence up to the supply. This tube, even though solidly anchored to the patient's wrist by tape, represents a substantial incumbrance and greatly limits movement of the patient. This problem is so acute that patients often sleep less well than they should out of worry that they will roll over and entangle themselves in the IV tube.

OBJECTS OF THE INVENTION

It is therefore an object of the present invention to provide an improved IV assembly.

Another object is the provision of such an IV assembly which overcomes the above-given disadvantages, that is which substantially eliminates the possibility of the patent getting tangled in the IV tube.

SUMMARY OF THE INVENTION

The instant invention is a holder used in combination with an IV stand having a post, an IV-liquid supply on the stand, and a tube extending from the supply to a recumbent patient adjacent the stand. The holder comprises a clamp body releasably secured to the post, an elongated pole having an inner end fixed to the clamp body and an outer end and extending horizontally from the clamp body and post, and a spring on the outer end of the pole connected to the IV tube between the patient and the supply and holding the tube up in the air above the patient.

Thus this system holds up the middle part of the IV tube like a fishing pole, but the spring allows the tube to move up and down considerably. As a result the patient can move about fairly freely, without worrying about the IV tube getting tangled in anything. The device is simple, of cheap construction, and certain to greatly reduce the problems inhering in use of an IV setup.

According to this invention the outer end of the pole is above the patient, to which end the pole is at least 24 in long. In addition the spring is a tension spring having an upper end secured to the outer end of the pole and a lower end releasably secured to the tube. This spring is stiff enough so that it can hold up the tube, but not so stiff that it prevents the tube from being pulled freely down.

The clamp body according to this invention is C-shaped and is provided with a screw for releasably locking it on the post of the IV stand. In addition this pole can telescope down to a length of about 10 in so that the IV stand carrying it can be moved about easily.

DESCRIPTION OF THE DRAWING

The above and other features and advantages will become more readily apparent from the following, reference being made to the accompanying drawing in which.

SPECIFIC DESCRIPTION

Figure 1:
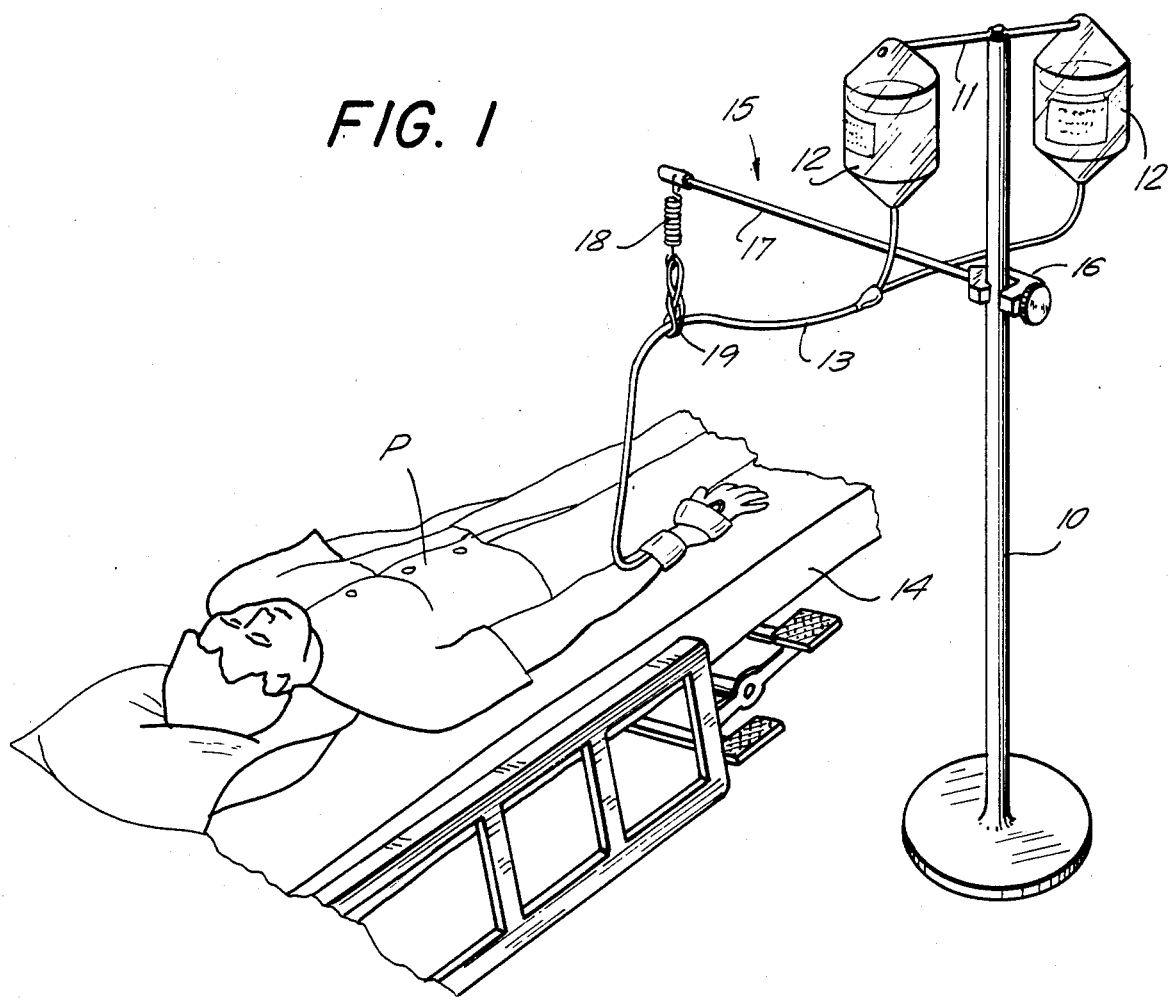
FIG. 1 is a perspective view of the system of this invention.

As seen in FIG. 1 a standard IV stand has an upright post 10 topped by an upper traverse 11 supporting two or more IV supply bags 12 from which a tube 13 extends to a needle implanted in the hand of a patient P in a bed 14 adjacent the stand. This equipment is standard and can be used to provide the patient P with blood, saline solution, or any intravenous liquid.

Figure 2:
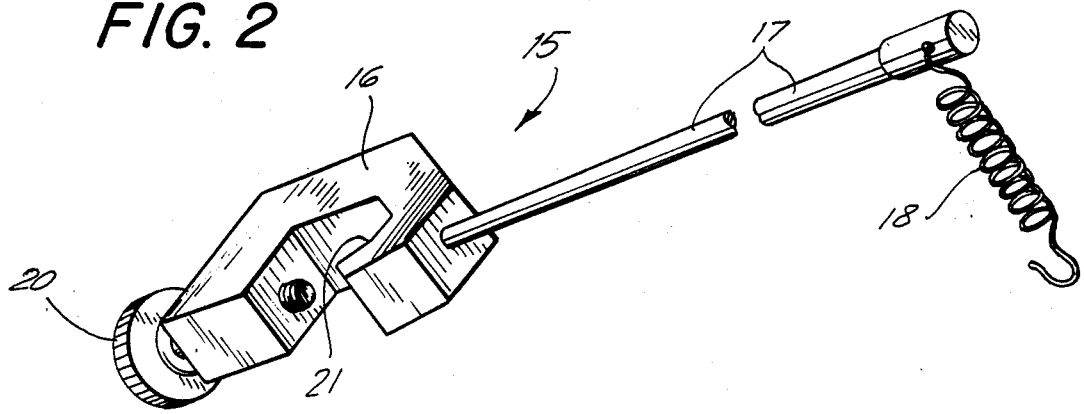
FIG. 2 is a large-scale perspective view of the IV holder according to the invention.

According to this invention and as also shown in FIG. 2, a holder 15 is provided which basically comprises a clamp body 16 and a three-part telescoping pole 17. The clamp body 16 is C-shaped and is provided with a knurled clamping screw 20 so that it can be connected as shown in FIG. 1 to the post 10 in a position with the pole extending horizontally therefrom over the patient P. The outer end of the pole 17 is formed with a throughgoing hole into which one end of a light coil-type tension spring 18 is hooked so that it hangs therefrom. The other end of this spring 18 is connected by a tie 19 such as a rubber band or twist-tie to the tube 13 between the supplies 12 and the patient P.

Figure 3:
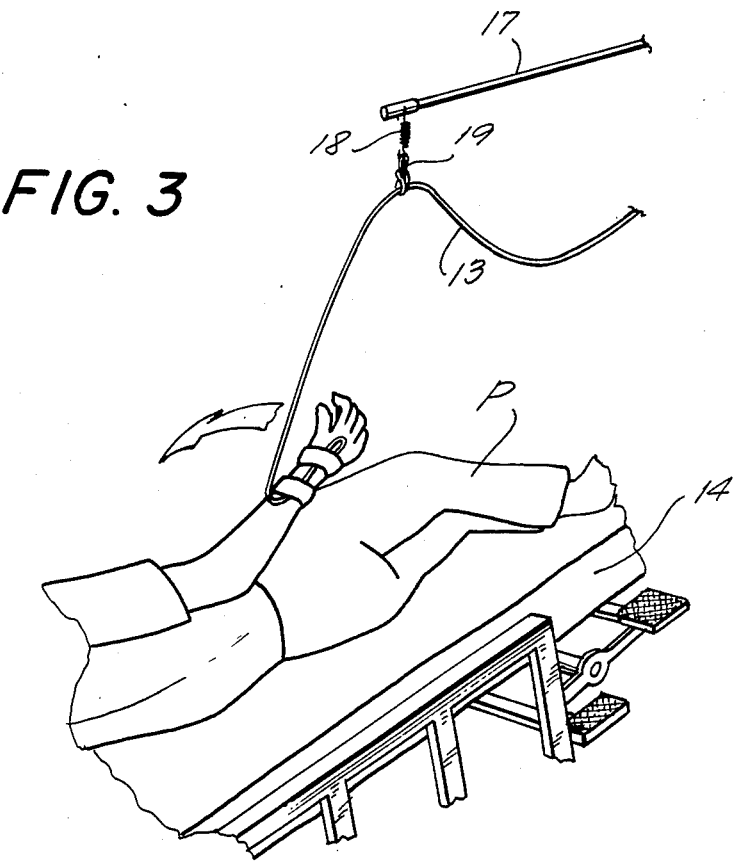
FIGS. 3 and 4 are partial perspective views illustrating how the system of this invention works.
Figure 4:
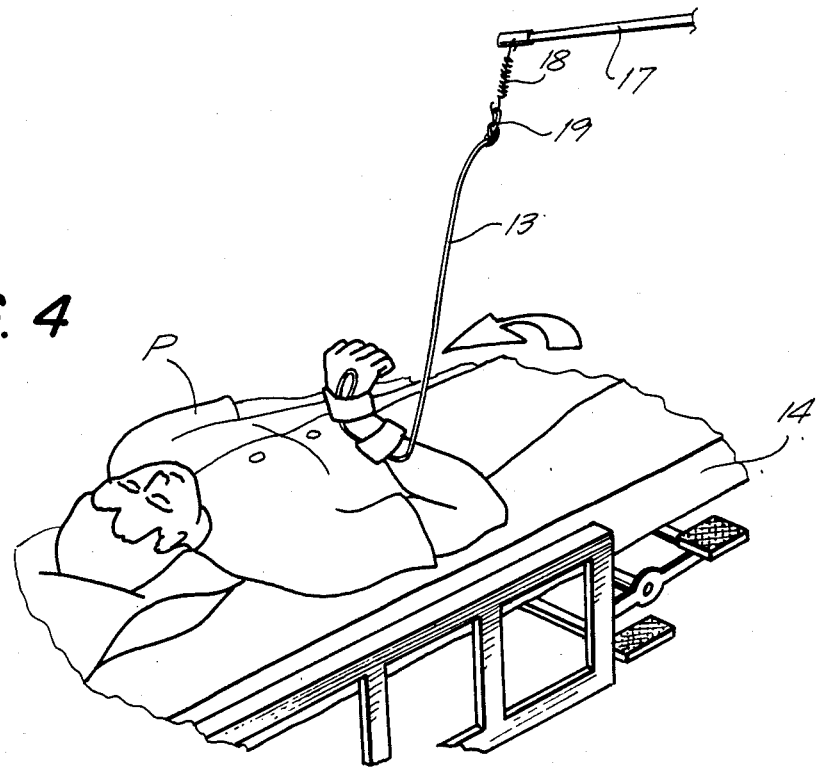

Thus the holder 15 keeps the tube 13 up out of the way, rather than trailing across the bed 14 as is normal. The spring 18 is sufficiently strong to hold up the tube 13, but light enough that as the patient moves the tube 13 can be pulled down. FIG. 3 illustrates how if the patient P rolls over, away from the stand 10, the tube 13 will easily follow him or her. Similarly as seen in FIG. 4 if the patient brings his or her arm up, the tube 23 can easily follow.

The clamp 16 has a V-shaped seat 21 aligned with the screw 20 so that the pole 17 will be solidly mounted in three-point contact, extending perpendicular to the post 10. This pole 17 can telescope to a total length of about 30 in so that it can hold the tube 13 well over the patient, but so that it can be collapsed, for instance when the IV stand is being wheeled through a doorway.

I claim:

1. An IV stand, comprising a post; means for mounting an IV-liquid supply on the stand; a tube extending from the supply and having a first end connected to the supply and a second end connectable with a patient and a portion spaced from and between said first and second ends;

a clamp body releasably securable to the post;

an elongated pole having an inner end fixed to the clamp body and an outer end and extending horizontally from the clamp body and the post so that said outer end can be positioned over a recumbent patient; and spring means supported by said outer end of the pole and connected to the IV tube at said portion and holding the portion such that the portion can be held up a recumbent patient by said spring means, said spring means being formed so as to allow movements of the tube which can be caused by a patient.

2. The combination IV-stand defined in claim 1 wherein the outer end is above the patient.

3. The combination IV-stand defined in claim 1 wherein the spring means is a tension spring having an upper end secured to the outer end of the pole and a lower end releasably secured to the tube.

4. The combination IV-stand defined in claim 1 wherein the pole telescopes to a length of at least 24 in.

5. The combination IV-stand defined in claim 1 wherein the clamp body is C-shaped and is provided with a screw for releasably locking it on the post of the IV stand.

6. The combination IV-stand defined in claim 1 wherein the pole telescopes from a maximum length of at least 24 in to a minimum length of at most 10 in.

7. The IV-stand as defined in claim 1, further comprising:
    means for connecting said spring means to the tube and including a tie.

8. The IV-stand as defined in claim 1, wherein the tube and the IV-liquid supply have a connection location therebetween at an elevation, said outer end of said pole being arranged at a height higher than said elevation of said connection.

* * * * *